United States Patent [19]

Murphy et al.

[11] Patent Number: 5,087,873
[45] Date of Patent: Feb. 11, 1992

[54] NON-INVASIVE, HIGH RESOLUTION DETECTION OF ELECTRICAL CURRENTS AND ELECTROCHEMICAL IMPEDANCES AT SPACED LOCALITIES ALONG A PIPELINE

[75] Inventors: John C. Murphy; Glenn S. Hartong, both of Columbia, Md.; Ralph F. Cohn, Worcester, Mass.; Patrick J. Moran, Arnold, Md.

[73] Assignees: New York Gas Group, New York, N.Y.; Southern California Gas Company, Elmonte, Calif.; Columbia Gas System Service Corporation, Columbus, Ohio

[21] Appl. No.: 690,290

[22] Filed: Apr. 24, 1991

Related U.S. Application Data

[60] Division of Ser. No. 504,100, Apr. 2, 1990, which is a continuation of Ser. No. 309,394, Feb. 10, 1989, abandoned.

[51] Int. Cl.$^5$ .................. G01N 27/26; C23F 13/02
[52] U.S. Cl. .................. 324/71.2; 324/529; 204/153.11; 204/404; 204/196
[58] Field of Search ............ 324/523, 529, 544, 551, 324/509, 71.2, 67, 326, 263; 204/196, 404, 153.11

[56] References Cited

U.S. PATENT DOCUMENTS

| | | | |
|---|---|---|---|
| 4,085,360 | 4/1978 | Howell | 324/67 X |
| 4,390,836 | 6/1983 | Bruce et al. | 324/529 X |
| 4,438,389 | 3/1984 | De Sa | 324/529 X |
| 4,438,401 | 3/1984 | Iwamoto et al. | 324/326 |
| 4,672,321 | 6/1987 | Howell | 324/67 X |

Primary Examiner—Jack B. Harvey
Attorney, Agent, or Firm—Kremblas, Foster & Millard

[57] ABSTRACT

Electrical current distribution in the soil surrounding a buried pipeline is detected by applying an AC electrical potential between the pipe and a buried electrode spaced from the pipe. The magnetic field at spaced localities along the pipe arising from currents transverse to the pipe is detected. Additionally, a potential containing a plurality of alternating frequencies is similarly applied to the pipe and the magnetic field induced by the resulting electrical current both along the pipe and transversely of the pipe is detected. The magnetic field is detected by correlation discrimination at spaced locations along the pipe and across the spectrum of the impressed frequencies. The detected data is used to determine the capacitance and resistance of the soil/pipe interface at localities along the pipe and to generate impedance plots which indicate characteristics of that interface.

4 Claims, 6 Drawing Sheets

FIG 8
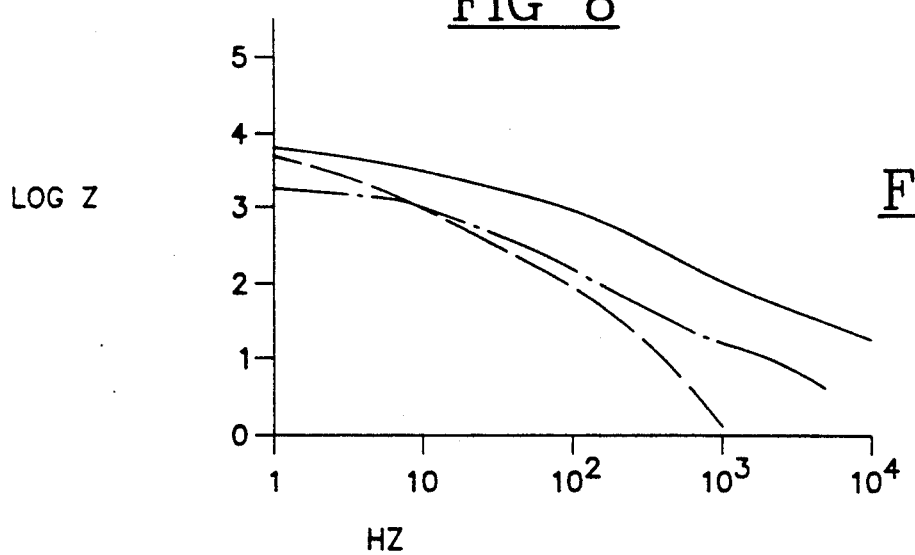
FIG 8A
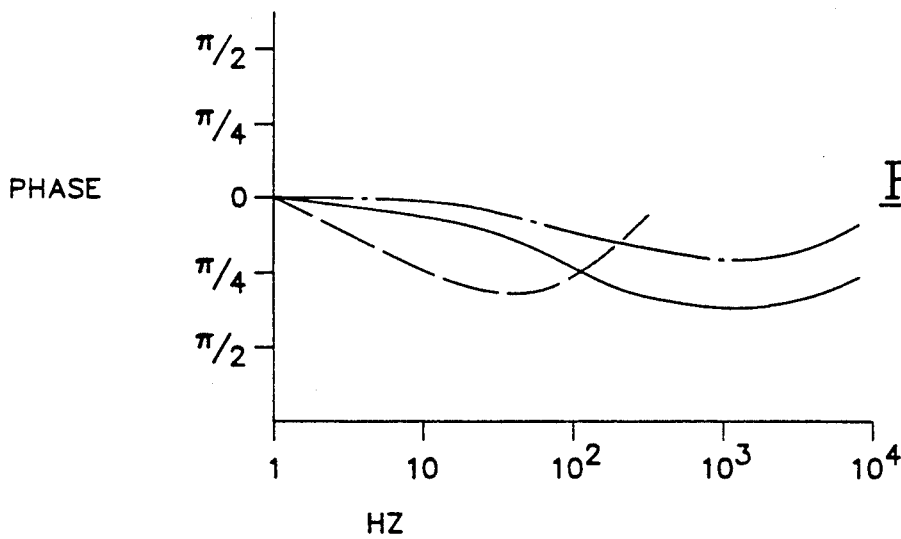
FIG 8B
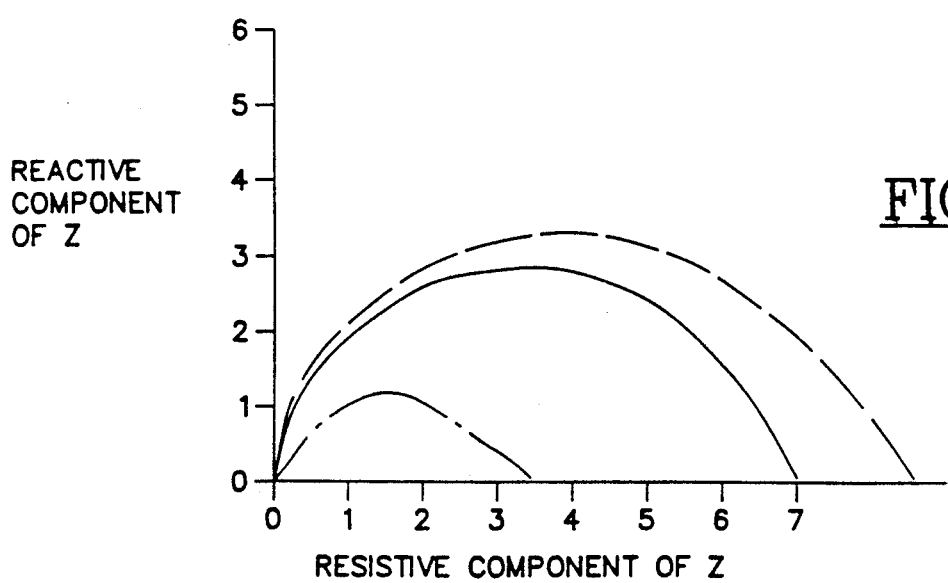
FIG 8C

NON-INVASIVE, HIGH RESOLUTION DETECTION OF ELECTRICAL CURRENTS AND ELECTROCHEMICAL IMPEDANCES AT SPACED LOCALITIES ALONG A PIPELINE

This is a divisional of application Ser. No. 07/504,100, filed Apr. 2, 1990, pending, which is a continuation of application Ser. No. 07/309,394, filed Feb. 10, 1989, now abandoned.

TECHNICAL FIELD

This invention relates generally to methods and apparatus for detecting the corrosion rate of a buried metallic pipe and for detecting current distribution and other parameters of an electrochemical circuit which includes a pipeline buried in a soil electrolyte and, more particularly, this invention relates to such methods and apparatus which are operable at spaced localities along the pipe to provide increased resolution for corrosion detection and current distribution monitoring without the necessity of excavation or local physical contact with the pipe.

BACKGROUND ART

Over a million and a half miles of pipeline are buried in the United States alone. Such pipelines are used to transport hazardous gases and liquids, many at high pressures on the order of 1000 psi. The majority of these pipelines involve natural gas transport. There are approximately 1000 pipeline failures reported each year with a few involving loss of life or significant property loss.

Corrosion of the pipe material is the main cause of pipeline failure. Corrosion is an electrochemical process involving metal oxidation and mass and charge transport between an electrode and a surrounding electrolyte. The charge transport implies that an electrical current flows between locations on the pipe and from the pipe to external electrodes. A metallic pipeline can be an electrode and the soil an electrolyte so that the pipeline buried in soil forms the elements of an electrolytic cell. Some corrosion arises from the naturally occurring processes at specific locations on the pipe involving electrical current flow into the ambient soil electrolyte via the corrosion reaction Corrosion is often additionally caused or accelerated by voltages applied to a local region of the pipe by man-made structures, including local transit systems, power distribution systems and other terrestrial sources of stray voltages and currents.

As a result, early detection and control of corrosion are necessary to maintain the integrity of a pipeline. To accomplish this, pipelines are periodically tested or continuously monitored for indications of corrosion activity and where necessary the electrochemical environment of the pipeline is modified by established control techniques.

Corrosion monitoring has been conventionally accomplished by conducting pipe to soil potential surveys to determine whether the potential difference between pipe and soil exceeds a specified threshold potential of 850 millivolts relative to the copper-copper sulfate couple and generally defined as adequate to prevent corrosion. Typically the pipe to soil potential measurements are accomplished using a copper/copper sulfate electrode half cell, wherein one electrode is connected to the pipe and the other is in contact with the earth above the pipe. Measurements of this potential are made at intervals from several feet to fifty feet or more. Monitoring of on-pipe currents is typically accomplished with the use of two electrodes physically bonded to the pipe at selected locations with a typical spacing of 200 feet.

These currently available methods suffer limitations. First, the pipe to soil corrosion potential method does not determine the corrosion rate. Rather, it indicates a condition where corrosion could take place electrochemically. In practice, pipelines exhibiting a corrosion potential greater than the $-0.85$ V$_-$/CuSo$_4$ limit cited previously have been found to be at risk of having unacceptable corrosion. Conversely, however, corrosion is a current phenomenon and the corrosion rate is proportional to the density of current between pipe and soil. There is a direct proportional relationship between the charge transfer processes responsible for the current and the metal mass transferred from the pipe electrode and the corrosion rate. In conventional electrochemical practice and in the present invention the central measured parameter is the ratio of the current density to the interfacial voltage between pipe and electrolyte viz the interfacial admittance or the inverse polarization resistance conventionally denoted as $R_p$.

Additionally, another limitation is that the measured pipe to soil potential is an average over a relatively large length of pipe because of the need for direct connection to the pipe to effect these measurements and the soil conditions from pipe to the earth surface. As a result, small regions of high corrosion rate which could lead to pipe failure may not be found.

Furthermore, the use of IR drop electrodes, which are physically bonded to the pipe at selected locations, while providing an effective measurement of pipe current, is expensive and is limited because of the expense and the need to provide specific monitoring sites. In particular, in present practice the two electrodes bonded to the pipe which comprise an IR drop pair, are spaced 200 feet apart. This means that only currents which flow continuously over this distance are monitored. In areas where many pipes are present or where current loss from the pipe is suspected, the spatial resolution of this technique is inadequate.

The industry has applied negative voltages between pipe and soil (cathodic protection) to achieve protection as illustrated in FIG. 1 However, there is considerable uncertainty as to the actual value of the potential at specific pipe locations and as to what voltage level provides adequate protection for the pipe.

There are several monitoring techniques known from conventional electrochemistry which provide information which is directly related both to the presence of active corrosion and to corrosion rate monitoring. Since corrosion is a process involving both mass and charge transfer between a corroding solid and its environment, all of these methods involve measurement of the exchange current and more particularly the interfacial impedance given by the ratio of the current to the interfacial voltage.

There has been a report of the use of a magnetic field detector to observe corrosion currents in a small electrochemical cell in a laboratory environment. However, the authors did not monitor corrosion rates, determine interfacial impedances or suggest that corrosion rates could be determined by magnetic field detection. This report consisted of an article entitled "Detection of Magnetic Fields Generated by Electro-Chemical Corrosion" in the August 1986 issue of the Journal of the Electrochemical Society. Detection consisted of observing temporal changes in naturally occurring corrosion currents flowing two dissimilar metals in contact with an aqueous electrolyte. There was no use of an impressed voltage across the cell such as would have been required to conduct classical electrochemical corrosion monitoring experiments. The lack of this impressed voltage also means that correlation based signal processing techniques cannot be employed. In our work these signal processing techniques are used to separate corrosion induced magnetic signals in practical pipeline applications from other magnetic signals associated with geomagnetic noise, magnetic materials and structures in the earth and environmental noise associated with automobiles and other moving objects.

Magnetic detection has also been used for many years for monitoring the current distribution on buried pipelines. An article entitled "Electromagnetic Techniques for Monitoring Pipeline Coatings", presented as paper 311 at a corrosion conference in March 1987, is a recent example of this type of application. In this paper N. Frost suggested that an AC potential can be impressed between a pipeline and an electrode buried in the soil and spaced from the pipeline. The current distribution of the current along the pipe is detected via a magnetic sensor which monitors the AC magnetic field produced by the AC current on the pipe. He illustrates the positioning of an inductive (coil) type magnetic sensor to detect on-pipe current and especially the decrement in on-pipe current which occurs as current leaks into the soil through the coating on the pipe. Using the change in the gradient of the on-pipe current with position above the pipe, he shows that coating breaks can be detected. What he has not shown is neither the detection of the transverse current leaving the pipe using magnetic sensing means nor the use of either the on-pipe or transverse current to determine the electrochemical impedance of the interface at the pipe where corrosion is taking place. The impedance measurement is essential to the application of magnetic sensing for corrosion detection and corrosion rate monitoring. Moreover, it is required for the quantitative determination of corrosion activity on the buried pipeline.

The Frost system is based upon the analysis that electrical current leaks preferentially from breaks or holidays in the protective pipeline coating because these exhibit substantially reduced electrical resistance. While a completely protected pipeline would exhibit a substantially constant current gradient along its length as a result of a relatively uniformly distributed current leakage, a holiday can be detected by a substantial change in the current gradient plotted as a function of distance along the pipe.

One problem with a system which looks only at on-pipe current is its low sensitivity. That problem arises because the differential changes in on- pipe current are relatively small compared to the total on-pipe current. Thus, the environmental noise, such as changes in the earth's magnetic field, stray currents, and cathodic protection currents, makes it difficult to utilize such a system.

The prior art has also suggested a variety of electrochemical measurement techniques for determining the interfacial impedance associated with the pipe/soil interface. For example, there is the Tafel extrapolation method in which the interface is perturbed with a DC voltage. The linear polarization method uses a small ramp function potential applied to the interface. The small amplitude cyclic voltammetry method uses a sawtooth which is a repeated ramp function. Others have suggested impulse measurements and the use of harmonic signal analysis.

An example of the latter system is "Electro-Chemical Impedance Spectroscopy". Electro-Chemical Impedance Spectroscopy, abbreviated EIS is a linear AC impedance method which is a conventional electrochemical technique for measuring the chemical condition at an electrode/electrolyte interface. Its application to measuring the corrosion rate at pipe/soil interface was suggested in a published report entitled "Effectiveness of Cathodic Protection" by Thompson, Ruck, Walcott and Koch and published in 1987. In this method a small amplitude, AC potential is applied by a source between a direct connection to the pipe and an electrode buried in the soil and spaced from the pipe. The amplitude and phase of the resulting source current with respect to the applied source voltage is detected for each of a plurality of source signal frequencies.

The total electrical current passing through the pipeline, soil, and electrode is assumed to be reasonably controlled by Randle's equivalent circuit or other equivalent circuit, several of which have been developed by the prior art workers. For example, equivalent circuits are discussed in an article in *Corrosion Science* entitled "Utilization Of The Specific Pseudo-Capacitance For Determination Of The Area Of Corroding Steel Surfaces" published in the August 1988 edition, volume 44, No. 8 and in a further article in the same issue entitled "Equivalent Circuits Representing The Impedance Of A Corroding Surface".

However, to adequately represent the current loss distribution on a large extended structure such as a pipeline, an equivalent circuit model such as that shown in FIG. 10 is required. At each location along the pipe there is an impedance value describing local current flow and hence local corrosion activity.

In EIS, the amplitude and phase data for the current at each frequency and applied potential are used to calculate a complex impedance for each frequency, including both the amplitude and phase of that impedance. This measured impedance of the circuit to which the AC source is applied for each of several frequencies may then be equated with the algebraic expression for the impedance of the equivalent circuit and these simultaneous equations are solved for values of the circuit elements. As is described in the prior art, the circuit elements, and particularly the interfacial resistance and capacitance along the pipe to soil interface provide indications of both interface condition, that is the presence or absence of holidays and corrosion, and also the corrosion rate. Often the process of impedance calculation is carried out under computer control.

A principal problem, however, with the EIS system and other prior art electrochemical systems described above is that they require physical contact with the pipe. Operationally, this is a major limitation when the pipe is under pavement or otherwise inaccessible. In addition, conventional measurements are applicable only to total currents passing through a relatively long spa of pipe. Thus, the measurements are essentially an average over a long span of pipe and do not provide information about the local condition of the pipe.

Thus, the disadvantages of conventional electrochemical methods for pipe corrosion detection are that they determine an average corrosion rate over an entire pipe length and therefore obscure small regions of high corrosion activity; they are not directly applicable under conditions of cathodic protection; and errors result from soil resistivity effects.

There is therefore a need for an improved system overcoming the above mentioned disadvantages of the current technology and providing for a non-contact system which can measure local current distribution and local impedance values.

BRIEF DISCLOSURE OF INVENTION

These local currents which flow transversely to the pipe generate an alternating magnetic field which is "solenoidal", that is the direction of the field is in the form of an annulus which encircles the current. As a result, if the component of the magnetic field along the spacial axis parallel to the current on the pipe is detected, it will be proportional to the current flowing transversely from the pipe to the soil.

In one aspect of the present invention an electrical potential which is alternating at at least one selected frequency is impressed between the pipeline and an electrode which is buried in the soil electrolyte and is spaced from the pipeline. The alternating electrical currents which are injected into the pipe by the electrical potential flow transversely away from the pipe and are distributed in the soil electrolyte at local regions along the pipe. Regardless of the axis selected, the magnetic field so determined is proportional to currents in the vicinity of the magnetic field sensor. This provides the ability to determine localized current distribution and hence interfacial impedances.

In another aspect of the present invention an alternating electrical potential which contains a plurality of frequencies is impressed between the pipeline and an electrode which is buried in the electrolyte and spaced from the pipeline. The alternating magnetic field which is induced by electrical currents injected into the pipeline by the alternating electrical potential is detected. The field is detected along at least one selected spatial axis at the frequencies of potential impression to detect electrical current at a local region, or at adjacent local regions, as a function of frequency. Thus, this method involves the application of a plurality of frequencies and their local detection by magnetic means in order to determine the interfacial impedance of the local region of the pipe and from the impedance determine the corrosion rate and other characteristics of the pipe/soil interface.

BRIEF DESCRIPTION OF DRAWINGS

FIGS. 8A-8C show representative impedance plots generated in accordance with the present invention.

Figure 1:
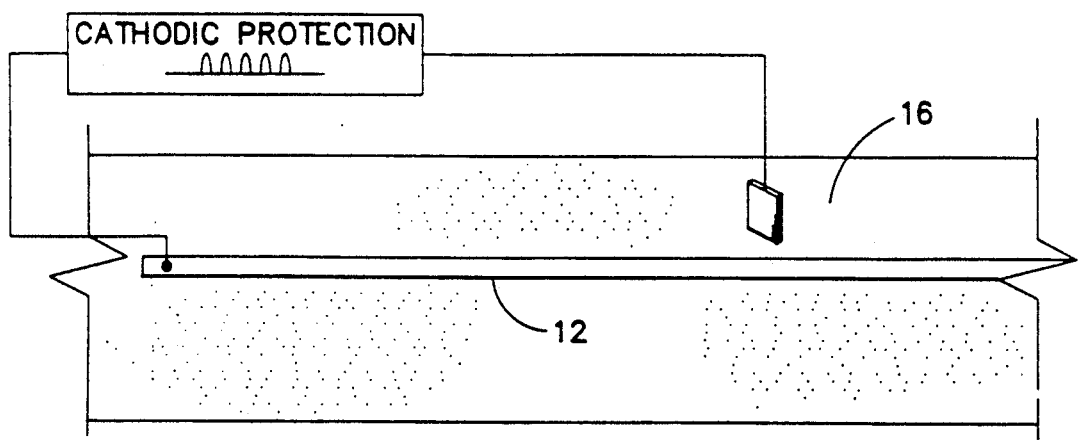
FIG. 1 is a diagrammatic view of a prior art pipeline system illustrating a pipeline with cathodic protection.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other circuit elements where such connection is recognized as being equivalent by those skilled in the art.

DETAILED DESCRIPTION

FIG. 2 schematically illustrates the principles of the present invention for detecting the current distribution and circuit impedance parameters with respect to an electrochemical circuit involving a pipeline buried in a soil. An alternating electrical potential is impressed by a potential source 20 between the pipe 22, buried in the soil electrolyte, and an electrode, which is also buried in the soil electrolyte and spaced from the pipe 22. This alternating source may be applied to an existing cathodic protection system 24 by applying its signal to the cathodic protection circuit and through it to the electrode 26. Alternatively it may be separately connected between the pipe at its end 28 and its own separate electrode 30.

The current injected into the end 28 of the pipe 22 is conducted mainly along the pipe. However, a distributed leakage current flows from the pipe into the soil along the length of the pipe and eventually returns to the source through the ground electrode 26 or 30. The magnitude of the current loss from the pipe at a selected position along the pipe depends upon the presence or absence of a protective, non-conductive coating, the conductivity of the coating, the capacitance of the coating, and the frequency of the impressed signal and importantly, whether a holiday or break in the coating exists and whether there is a low resistance path to an interfering electrode or stray current source.

The reduction of on-pipe current per unit length of pipe and the increase of off-pipe current is largest at locations where there is a holiday or short present. By measuring the rate of change of on-pipe current or off-pipe current, which are complementary, as a function of position along the length of the pipe, holidays nd shorts can be located even when there is a generalized distributed current loss through the protective coating at other regions of the pipe. In addition, the properties of the interface between the pipe and the soil electrolyte can be determined in accordance with the present invention for spaced local regions along the pipe for coated and bare pipes and the current distribution for spaced locations along the pipe, both on-pipe and off-pipe, can be mapped.

These principles are illustrated in FIG. 2. In FIG. 2A a corroded holiday 32 causes the flow of off-pipe currents at an increased current density in the region of the corrosion 32.

Figure 2A:
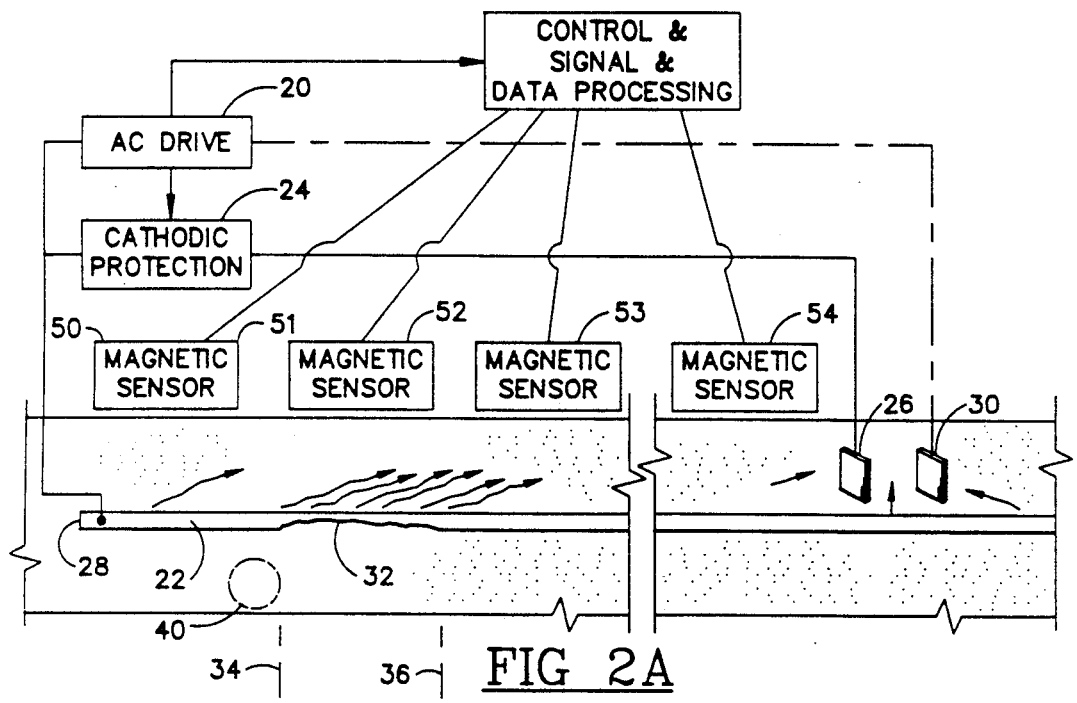
FIG. 2A is a diagrammatic view illustrating the preferred embodiment of the invention illustrating the circuitry and the placement of the magnetometers.
Figure 2B:
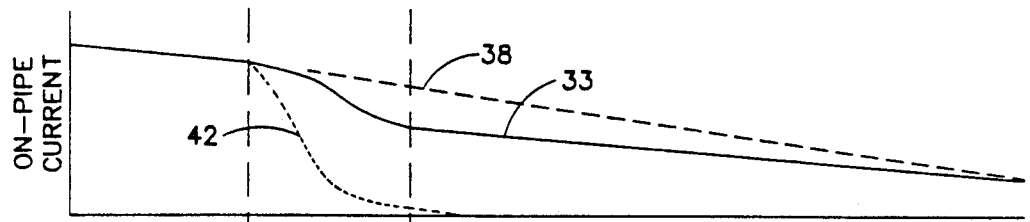
FIGS. 2B, 2C, and 2D are graphical plots of current and differential current distributed along the pipeline.

FIG. 2B is a plot representing the on-pipe current as a function of lineal distance along the pipe. The solid line 33 represents the on-pipe current. It illustrates that the on-pipe current decreases within the region between the boundaries 34 and 36 of the corrosion of the holiday 32 because of the increase of the distributed current loss within that region.

If there were no holiday, corrosion or other defect along the length of a protectively coated pipe, then the on-pipe current distribution would continue at a relatively constant slope, as illustrated by the dashed lie 38.

The current leakage would be even greater if there were a short in the vicinity of the corrosion 32. For example, if another pipe 40 extended from a location near the corrosion 32 to a region near the electrode 26 or 30, then a considerably lower resistance path than found through the soil would exist in the circuit and the distributed current loss at the corrosion 32 would be substantially increased. If that occurred, the on-pipe current would be as represented by the phantom plot 42 in FIG. 2B.

One difficulty with the detection of on-pipe current is that the changes in on-pipe current are relatively small since a majority of on-pipe current continues through the considerably lower resistance pipe. For example, the solid line plot 33 of FIG. 2B is substantially exaggerated in order to illustrate the principle.

Figure 2C:
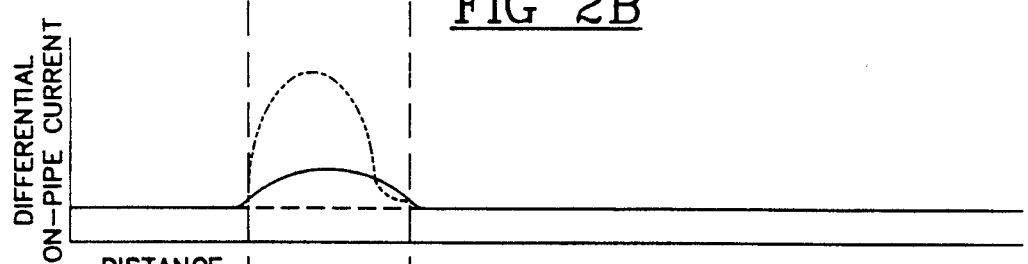

The detection may be somewhat enhanced by plotting the current gradient, that is the current differential, along the pipe as illustrated in FIG. 2C. For example, the solid, dashed and phantom plots of FIG. 2C represent plots of the differential of the corresponding lines in FIG. 2B. These too are difficult because a reasonably accurate plot of a gradient is completely dependent upon a reasonably accurate measurement of the currents themselves and therefore even when the differential is plotted, the system is not accurate.

A measurement made by the EIS system would also present an average for the entire length of the pipe from its end 28 to the region at the opposite end associated with the position of the electrode 26 or 30. In the present invention, however, as illustrated in FIG. 2, a magnetic sensor 50, such as a magnetometer, may be used to detect the alternating magnetic field induced by the electrical currents which are injected into this circuit by the electrical potential which is applied to the pipe 22.

In one embodiment of the present invention the magnetic sensor 50 is aligned to detect the soil currents which are distributed in the soil and flow transversely away from the pipe at each local region below the position of the magnetic sensor. The magnetic field is detected along the spatial axis which detects the transverse current flow, for example along an axis which is parallel to the pipe. The current flow is detected at the frequency of the impressed potential. Because the off-pipe currents are relatively small in most regions where the pipeline is protected and its protective coating is intact, the presence of a holiday is more easily detected because a holiday will produce an increase in local transverse currents many times the local transverse currents which exist where the protective coating is still intact. The magnetic sensor 50 can also be aligned along other spatial axes and sensors to detect magnetic field components along all three dimensions can be used.

Figure 2D:
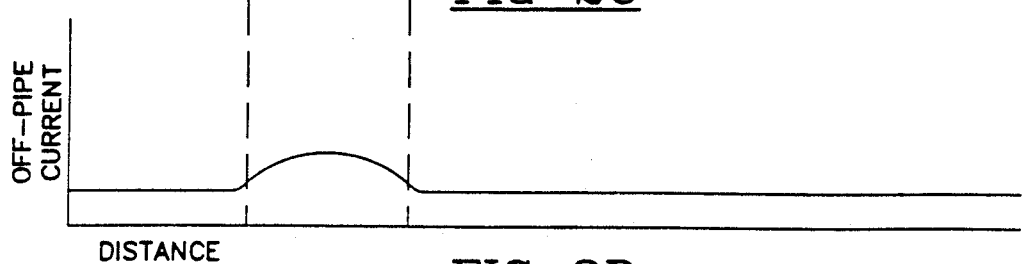

FIG. 2D is a graph illustrating the transverse current distribution along the pipe 22 illustrated in FIG. 2A. For example, if a current is injected into the end 28 of the pipe 22 and a five percent reduction of on-pipe current occurred within the range between boundaries 34 and 36, the on-pipe current might, for example, decrease 5%, but the off-pipe current might increase 500%. Actual current values depend on the length of the pipe being inspected and the area corroding. Corrosion current densities of 100 microamps per square centimeter are large typical values, hence if the corroding area is 1 meter square the transverse current at this site is 1 ampere.

It is important that the potential impressed at the alternating frequency in order to conduct the test described above cause only small perturbations of the existing ambient currents which exist in the absence of the AC signal. The perturbations must be sufficiently small to avoid any significant depolarization of the corroding object/electrolyte interface away from its steady state ambient condition. Otherwise, significant depolarization will change the chemical and therefore the electrical parameters of the corroding interface and the detected currents will not be an accurate indication of the corrosion currents.

In current mapping the frequencies preferably used are typically 0.02 Hz to 1 KHz. In corrosion rate monitoring the frequencies needed for determining the parameters in the Randle Model are typically 0.02 Hz–1 KHz, but might go higher to 10 KHz.

Figure 3:
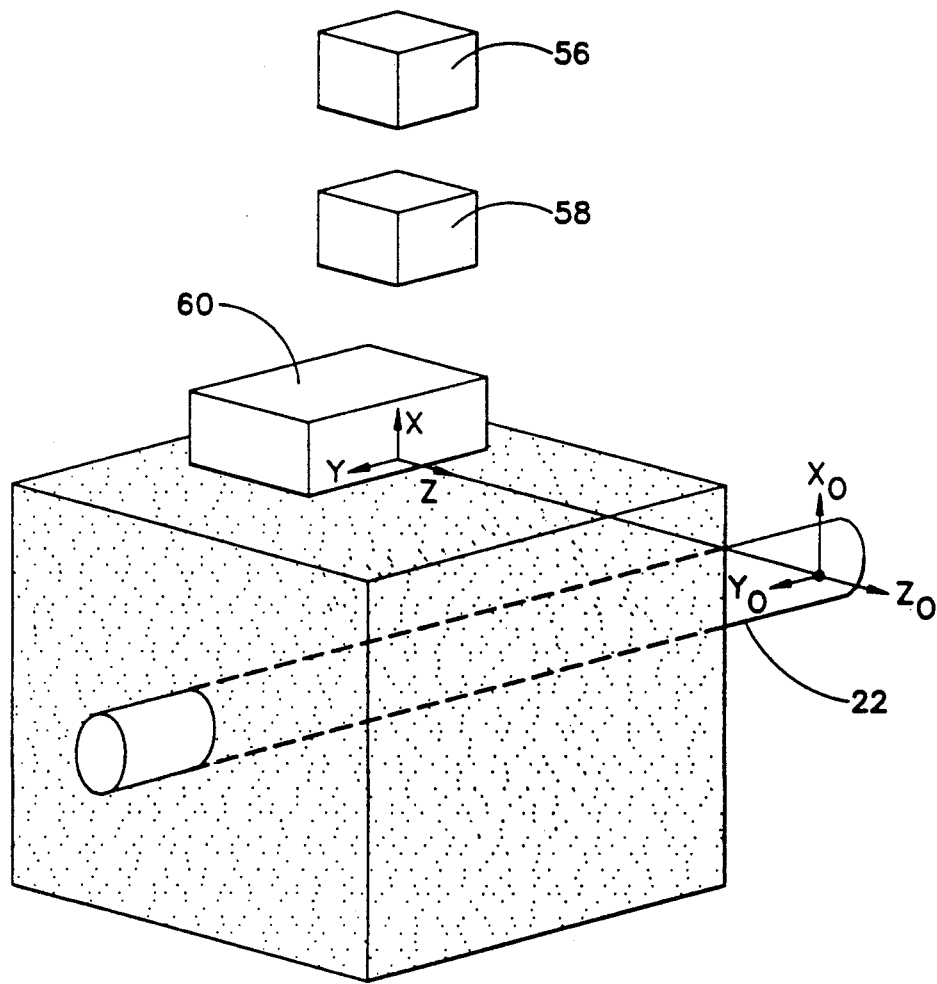
FIG. 3 is a diagram illustrating three-dimensional coordinates and magnetometer positioning for a pipeline buried in the soil and a magnetometer which can measure the field component in all three dimensions.

FIG. 3 illustrates a coordinate system which is useful for description of the invention. The coordinate system may be defined to include a Y axis, with reference point $Y_0$, along the axis of the buried pipe, an X axis, with reference point $X_0$, which is vertical and perpendicular to the Y axis, and a Z axis, with reference point $Z_0$, which is horizontal and perpendicular to the other two axes. The transverse distributed currents leaking from the pipe 22 have components of flow, principally parallel to the X and Z axes. Thus, if a magnetometer is positioned directly above the pipeline, the vertical current flow along the X axis may be detected by detecting the B magnetic field, parallel to the Y and Z axes and the horizontal component of transverse current may be detected by detecting the B field parallel t the X and Y axes. Additionally, the on-pipe current may be detected by detecting the current parallel to the X and Z axes.

Magnetometers are currently available and commercially sold for use in the present invention. For example, a magnetometer which may be used is a triaxial low temperature SQUID (Superconducting Quantum Interference Detector), manufactured by Biomagnetic Technologies Inc., Model GMP 45. This magnetometer has a frequency response from DC to 1,000 Hz, a dynamic range of 140 dB, and an output noise of less than 1 milligamma RMS per square root Hz. This magnetometer is preferred for the corrosion rate measurements to be described below.

Another magnetometer is the monoaxial Scintrex, Model MFM-3 flux gate magnetometer, which has a frequency response of 0–10000 Hz, a maximum response of + or − 100 gamma and an output noise at 0.01–1.0 Hz of 10 milligamma peak-peak V per square root Hz and at 1–1000 Hz less than 1 milligamma/V per square root Hz. This implies a dynamic range of 80 db for corrosion rate measurements. A third magnetometer is preferred for current mapping and is Model SDM manufactured by Electromechanical Design Services, Inc. It features four magnetometers in a gradiometer arrangement with a frequency response of DC to 2500 Hz. It has an output of + or − 50,000 gamma and an output noise at 0.1–20 Hz of less than 0.1 gamma peak to peak implying a dynamic range greater than 100 db. This final unit is capable of detecting the magnetic field component along all three-dimensional axes and additionally it is able to detect a signal which may effectively be subtracted from the readings of the three axes to subtract out and eliminate the ambient magnetic field which is not due to the injected currents, but rather arises from surrounding noise, such as the earth's magnetic field, and other ambient noise in the measuring environment.

Alternatively, as illustrated in FIG. 3, a pair of magnetometers may be positioned at two positions 56 and 58, illustrated in FIG. 3, which are at two different radii from the pipe so that the field measured at one position may be subtracted from the field measured at the other to eliminate these ambient magnetic fields and to normalize for variations in pipe depth. Preferably, however, the multi-axis magnetometer is positioned at 60, as illustrated in FIG. 3, to detect the magnetic field along all three-dimensional axes. The data from the multi-axis magnetometer is then computer analyzed in accordance with the methods known to those skilled in the art and those described in this patent.

In a systematic testing of a pipeline, the first step is to do a survey of current distribution to find holidays along the pipe. To accomplish this, the current is mapped at spaced locations along the pipe in order to find the places with excessive transverse current loss from the pipe. After the specific location of excessive current leakage has been determined, further testing and analysis is done in accordance with the present invention to determine the electrical impedance parameters associated with the regions of high current loss and from that determine the corrosion rate at these suspect locations. The impedance parameters are obtained using an analysis which is similar to previous electrochemical impedance measuring techniques except that, with the present invention and its use of magnetic detection, resolution is greatly enhanced because the impedance parameters of local regions may be determined. This enables the measurement of differential or incremental impedance changes between a series of adjacent local pipe regions so the corrosion rate at small local regions may be determined.

In addition to mapping current leakage which arises from the circuit characteristics of the pipeline and its coating, holidays, and corrosion, the currents due to cathodic protection and stray currents may also be separately mapped.

Cathodic protection is commonly applied by a full-wave rectified 60 Hz sinusoid. Thus, the characteristic frequency of typical cathodic protection is 120 Hz. As a result, detection and mapping of on-pipe or off-pipe current flow can be accomplished by detecting the alternating magnetic field at 120 Hz. Similarly, stray currents arising from power distribution systems or subways operating at 60 Hz can also be detected by detecting the alternating magnetic field at 60 Hz. Additionally, stray currents from DC systems, such as a DC operated subway system, may also be detected. This may be accomplished because it has been found that so called DC systems nonetheless produce voltage and current variations which vary with time at a low frequency in the range of 0.1 to 2 Hz. Current variations within that frequency range may be detected and attributed to those stray current sources. Thus, the current for each of these sources which has a characteristic frequency can be separately mapped and this permits identification of the principal source of these currents which may also contribute to the electrochemical corrosion process. If the cathodic protection current is at the same frequency as another stray current, for example both are at 60 Hz, the cathodic protection current may be turned off to distinguish it from the other currents.

Figure 4:
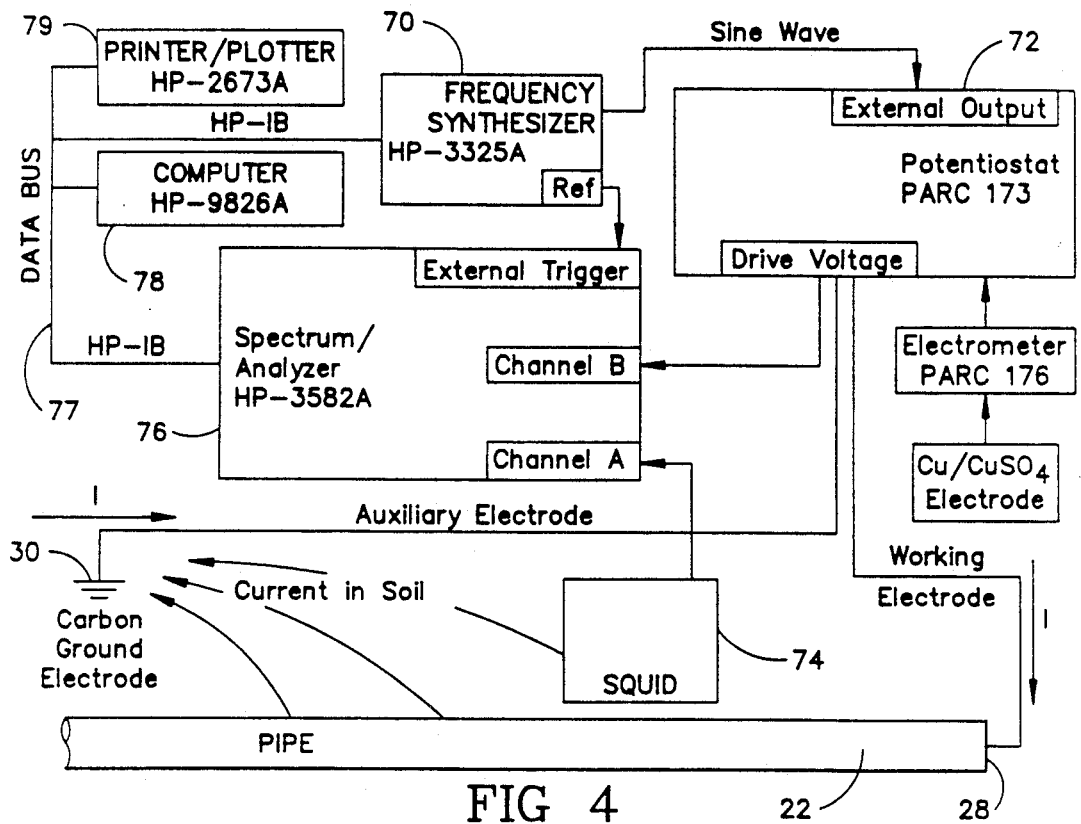
FIGS. 4-7 are block diagrams illustrating alternative embodiments invention.

FIGS. 4-7 illustrate circuits which are useful for these purposes. FIG. 4 illustrates a block diagram of a circuit useful for practicing the present invention. A signal at the frequency to be injected into the pipe is generated by a frequency synthesizer 70. The frequency synthesizer is of conventional nature, such as a Hewlett-Packard Model HP-3325A or equivalent, and has a frequency range of 0.02 Hz to 20,000 Hz with an AC voltage output of 1 millivolt to 100 millivolts RMS. That signal is applied to the input of a potentiostat 72 for maintaining a constant voltage amplitude output which is applied between the end 28 of the pipe 22 and a buried electrode 30 to impress the drive voltage upon the circuit including the buried pipe and the soil electrolyte. The potentiostat, for example a potentiostat manufactured by Princeton Applied Research, Model PARC 173 or PARC 273 or one manufactured by Kepco, Model BOP 36-6M or an equivalent, desirably has a frequency range of DC to 20,000 Hz and an output impedance of 120 microohms series resistance and 50 microhenries series inductance.

A proportional signal is also applied to channel B of a dual channel spectrum analyzer from the potentiostat 72. A suitable spectrum analyzer is one commercially available, for example Hewlett-Packard, Model HP-3582A or equivalently one available from Princeton Applied Research, Model PARC-5204 or other equivalent spectrum analyzer. It desirably has a range of 0.02 Hz to 25,000 Hz and a dynamic range greater than 70 dB and a noise floor of $-120$ dB V. The output from the magnetometer 74 is directed to channel A of the same spectrum analyzer. In this manner the spectrum analyzer has available both a reference potential, which is proportional to the AC potential which is applied between the pipe and the ground electrode 30 and a signal which is proportional to the magnetic field detected by the magnetometer 74.

The spectrum analyzer 76, a computer 78, a printer plotter 79, and the frequency synthesizer 70 are all connected by means of a data bus 77. In this manner digital data may be sent from the computer to the other devices, which are also attached to the bus, for controlling those devices and may also be sent by those devices to the computer in the conventional manner. For example, the computer controls the frequency of the frequency synthesizer and receives spectrum data from the analyzer 76 in response to appropriate digital instructions.

The computer we have used is a Hewlett-Packard 9000 series or an equivalent, such as an IBM PC or Macintosh II or any other of the 286 or 386 series machines.

The printer we have used is a Hewlett-Packard Model HP-2673A or HP-82162A.

The spectrum analyzer and computer have been selected and programmed to perform coherent averaging and correlation discrimination of these signals. While these are conventionally known signal detection and processing techniques they are particularly advantageous when combined with the other process steps of the present invention. These techniques are particularly advantageous because two problems are simultaneously present in attempting to apply the present invention. Firstly, the magnetic fields which are detected are submerged in magnetic noise which is of greater amplitude than the signals themselves and secondly, the measurements made by the present invention are inherently transfer functions, such as an impedance, relating two different signals. For example, if the decrement in on-pipe current is to be examined, the relationship of on-pipe current between two spaced locations provides an indication of off-pipe current. In a complimentary manner the relationship of directly measured transverse current at one location to directly measured transverse current at another location provides an indication of whether or not a holiday exists. Similarly, and as subsequently described, when electrochemical impedance techniques are utilized for measuring the interfacial impedance in order to determine the corrosion rate, impedance is itself inherently a transfer function. The interfacial impedance is based upon the transverse pipe current.

Correlation discrimination is a known prior art technique for improving the signal to noise ratio and therefore it is only briefly described. With correlation discrimination the spectra of each of two signals are compared in a manner which detects from the second signal the signal information which correlates with the first signal. More particularly, time samples of the two signals are Fourier transformed to provide Fourier components for each of the signals. The amplitude of those Fourier components in the second signal, which are also found in the first signal, at the phase they are found in the first signal are determined, thus providing an output signal which improves the signal/noise ratio and effectively represents a transfer function between the two signals.

The magnetometer of the circuit illustrated in FIG. 4 is positioned at each of a plurality of spaced positions along the pipe 22 and the field data measurement is taken at each position. In this manner the relative current amplitude at each location may be simply plotted as a function of location to provide a plot such as illustrated in FIG. 2. Data for determining interfacial electrochemical impedance parameters is obtained as described below.

Figure 5:
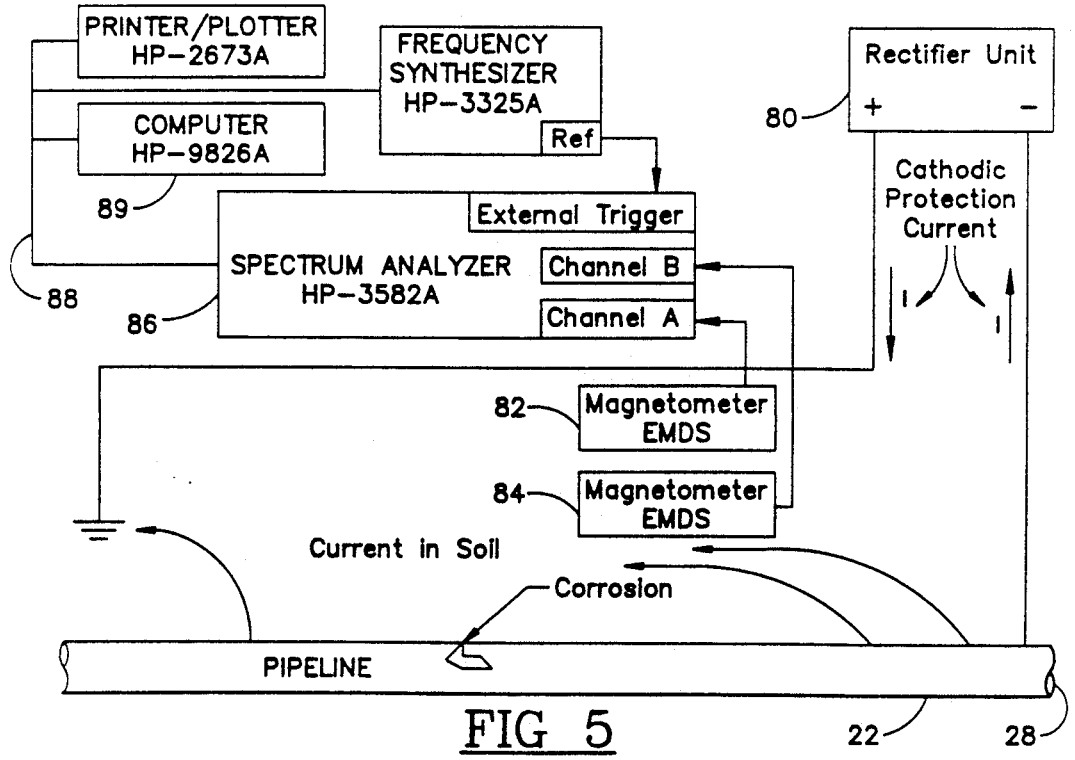

FIG. 5 illustrates a similar circuit, but one in which a separate alternating potential source is eliminated. This circuit is used for detecting a stray current, such as the cathodic protection current. In FIG. 5 the cathodic protection rectifier source 80 is illustrated as connected to an end 28 of the pipe 22 and it operates as an already existing alternating potential source. Although a single magnetometer could be used, we prefer to use a pair of magnetometers 82 and 84 of spaced radial distances from the pipe 22 to normalize for variation in pipe depth. The output from each magnetometer 82 and 84 is applied respectively to channels A and B of the spectrum analyzer 86. The spectrum analyzer data is transferred on the data bus 88 to the computer 89 for analysis.

This provides conventionally known amplitude and phase data, such as is conventionally obtained by performing a fast Fourier transform upon the signal detected by the spectrum analyzer. This spectrum showing the amplitude and phase of the field as a function of frequency can then be used to determine the current components arising at the 120 Hz frequency of the cathodic protection rectifier source 80. The same analysis can be used to detect and separate the currents arising from 60 Hz power distribution signals. Additionally, the identical technique can be used to determine currents arising from sources which vary in the frequency range of 0.1 to 2 Hz, such as is typical of DC operated transit systems. This data is conveniently used for mapping the currents attributable to these particular source along with the pipe. This is done by simply taking repeated measurement at spaced locations along the pipe, storing the measurement data and then using it for mapping the transverse currents as a function of position along the pipe.

Figure 6:
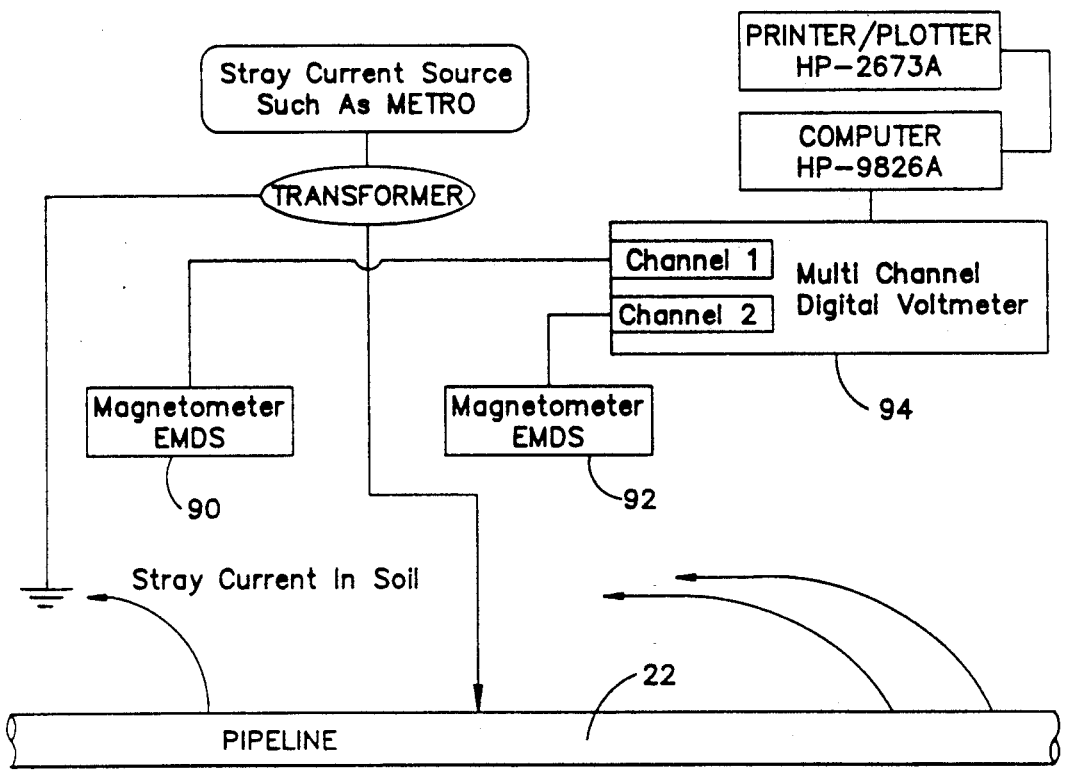

FIG. 6 illustrates a similar circuit for mapping stray currents or other currents which features a pair of magnetometers 90 and 92 which are spaced at adjacent local positions along the pipeline 22. This enables the magnetic field detected at two adjacent local positions to be differenced in order to obtain both the field differential between the two local positions and to cancel some magnetic noise, such as geomagnetic fields. The magnetometer outputs may be directed to the respective channels of a spectrum analyzer instead of the digital voltmeter 94 which is illustrated. The data is then analyzed at the frequency of the stray current. The differential current may be plotted. In this manner a plot, such as that illustrated in FIG. 2C, may be plotted and this may be accomplished for on-pipe current, off-pipe current or each spatial component of current so that the differential may be plotted to better reveal the locations of major holidays.

The circuit of FIG. 6 is further simplified an its cost reduced by using a multi-channel digital volt meter 94 instead of the spectrum analyzer. This is possible for relatively DC stray currents. That is, this is possible for DC currents which vary relatively slowly and are near DC. The computer simply subtracts or else the multi-channel digital volt meter subtracts the voltages from the two magnetometers, which are proportional to their detected magnetic fields. In this manner the signal used by the computer represents the difference in the magnetic field between the positions of the magnetometers 90 and 92.

After the currents associated with the pipeline have been mapped to determine positions with excessive leakage current, the locations of excessive current may then be further analyzed in accordance with the present invention.

The prior art literature not only hypothesizes and tests equivalent circuits for the circuit consisting of the pipeline, soil and the electrode, but has additionally analyzed the electrical characteristics of this circuit as they are affected by the condition of the soil/pipeline interface. It has been found, for example, that at a simple break in the pipeline protective coating, the resistance of the interface decreases because of a break in the insulative coating. Furthermore, it has been found that, if there is little or no corrosion at the position of such a holiday, the capacitance of the interface decreases because of the direct contact with the electrolyte and the absence of the coating which would otherwise form a dielectric between the pipe metal and the soil.

The prior art literature has further shown that the corrosion interface produces an increase in capacitance such that a substantially corroded surface produces a substantially increased interfacial capacitance substantially greater than the capacitance in the presence of a protective coating. For example, it has been experimentally determined that the capacitance of a corroding interface is on the order of 100–300 microfarads per square centimeter in certain soils. We have found, however, that for a broader range of soil compositions the capacitance of a corroding interface may be within the range of 1 to 40,000 microfarads per square centimeter. As a result, it is possible to experimentally determine the capacitance per unit of pipe surface for a variety of combinations of pipe materials and soil combinations.

From this it is apparent that the capacitance of a unit area of pipe surface may be experimentally determined. Thereafter, the total capacitance of a local holiday may be measured in accordance with the present invention. The area of the corroding soil surface may then be determined by simply dividing the total capacitance by the capacitance per unit area.

Therefore, a measurement of the capacitance of a corroding holiday can be used to determine the area of the holiday and additionally a measurement of the resistance of the soil/pipe interface can be utilized to mathematically determine the corrosion rate. The prior art literature has shown that the corrosion current may be expressed by the equation:

$$i_{CORR} = B_a B_c / [2.3(B_a + B_c) R_p]$$

where $i_{CORR}$ is the corrosion current density of the surface of the specimen.

The above equation is essentially the product of the resistance per unit area $R_p$ of the soil/pipeline interface multiplied by a conversion constant. The conversion constant involves the product of the respective Tafel slopes divided by a sum of those slopes and therefore the calculation of corrosion rate is not significantly affected by errors in the values of the Tafel slopes. The prior art has further shown that the value of the entire conversion constant is generally between 0.01 and 0.02 volts and therefore the resistance of the soil/pipe interface may be multiplied by a conversion constant within that range to obtain a good approximation of the corrosion current density $i_{CORR}$.

The prior art literature further shows that the relationship for converting to the conventional mils per year corrosion rate to determine the corrosion rate for steel, for example, is:

$$mpy = i_{CORR}/2.2$$

where the corrosion current density is expressed as microamps per square centimeter.

The entire resistance of the interface may be determined using the present invention and multiplied by the area of the interface, as determined by the capacitance as described above, to obtain the resistance per unit area of the corroding interface and from that the corrosion rate.

In order to determine the total interfacial resistance $R_p$ and the interfacial capacitance $C_p$, so that corrosion rate and corrosion surface area may be determined as described above, an alternating electrical potential containing a plurality of frequencies is impressed between the pipeline and an electrode which is buried in the electrolyte and spaced from the pipeline. The alternating magnetic field induced by electrical currents injected into the circuit by that electrical potential is detected along at least one spatial axis. It is detected at the frequencies of potential impression at local regions of the circuit. For example, the impressed potential may be the sum of a series of discrete frequencies which is applied to the pipeline. The magnetometers and spectrum analyzers then detect the resulting magnetic signal at a local position along the pipe for each of these discrete frequencies. Amplitude and phase data detected at the location for each of these frequencies may then be used by the computer to determine the values of the circuit elements in the selected equivalent circuit. For example, the plurality of algebraic expressions representing the impedance may be equated to the impedance measured and stored in the computer in the form of an amplitude and phase for each frequency to provide a series of simultaneous equations which may be solved for the circuit elements of the equivalent circuit.

Additionally, such data may be taken for each of a series of several locations along the buried pipe spaced, for example, every two meters. The detected values for adjacent spaced locations may be differenced to obtain differential values, such as differential impedance for each increment between the spaced locations.

Figure 7:
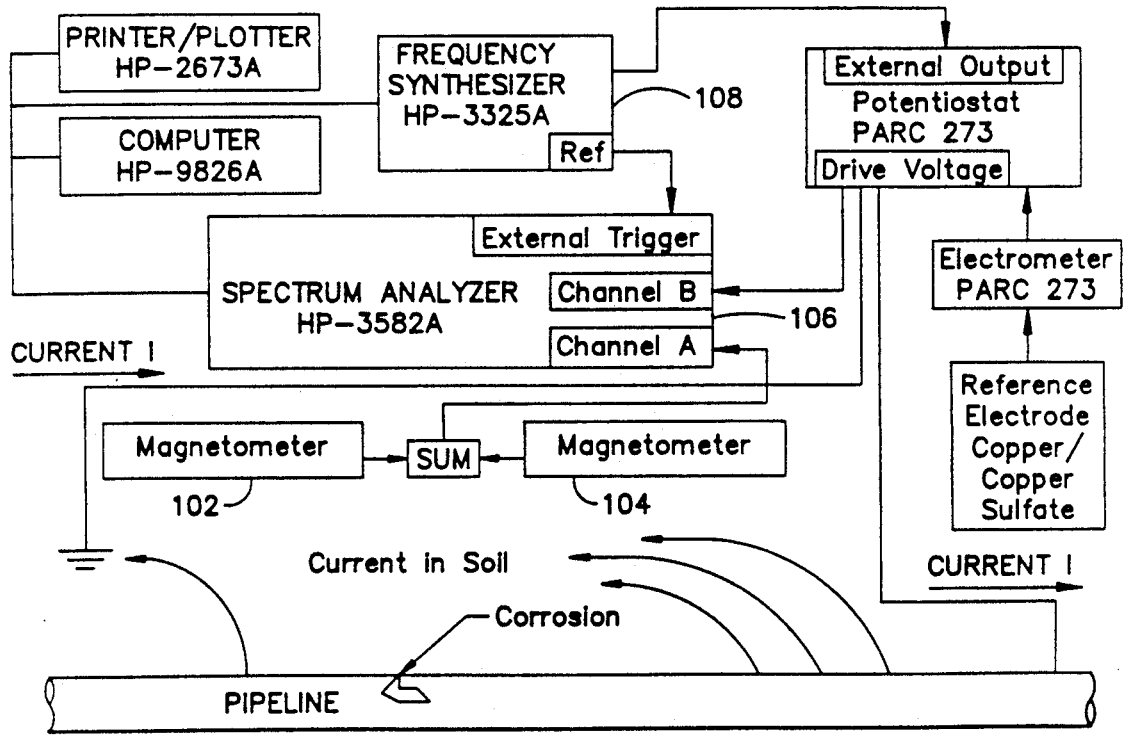

Even more desirably the circuit of FIG. 7 may be utilized which is like the circuit of FIG. 4 except that a pair of magnetometers are positioned at longitudinally spaced locations along the pipe and are connected to a summing junction so that a signal proportional to the difference in their detected fields is applied to channel A of the spectrum analyzer 106. In this manner the circuit of FIG. 7 is able to directly detect the incremental impedance between two spaced locations along the pipe.

It is more effective to apply a broader spectrum of frequencies rather than select and sum discrete frequencies. For example, the frequency synthesizer, such as frequency synthesizer 108 in FIG. 7, may be controlled by the computer to sweep from a lower frequency to a higher frequency and then to detect and store data representing the amplitude an the phase of the magnetic field as a function of the sweep frequency. This data is then used as described above or using other known analytical techniques to determine the values of the circuit elements of the equivalent circuit and especially to determine the interfacial resistance and capacitance associated with that circuit.

Of course, other methods to obtain a plurality of frequencies are also available. One is to apply a random noise generator and another is to periodically apply a pulse between the pipe and the buried electrode to induce a magnetic field containing a broad spectrum of frequencies. The magnetic field is then recorded as a function of time and a fast Fourier transform is performed on the recorded data to obtain the amplitude and phase for each of a plurality of frequencies contained within the detected signal generated by the pulse. In addition to using the stored amplitude and phase data, which is a function of frequency, for computing the values of $R_p$ and $C_p$, that data may also be used to generate impedance plots.

FIG. 8 represents such impedance plots. FIG. 8A is a Bode impedance amplitude plot and FIG. 8B is a Bode phase plot. FIG. 8C represents a Nyquist impedance plot. Preferably these plots are generated for a differential impedance measured in accordance with the present invention at adjacent spaced locations along the pipe. They can be used to qualitatively and quantitatively analyze the measurements to determine the presence or absence of a holiday and whether the holiday is substantially corroded or simply an uncorroded break in the pipe.

Figure 9:
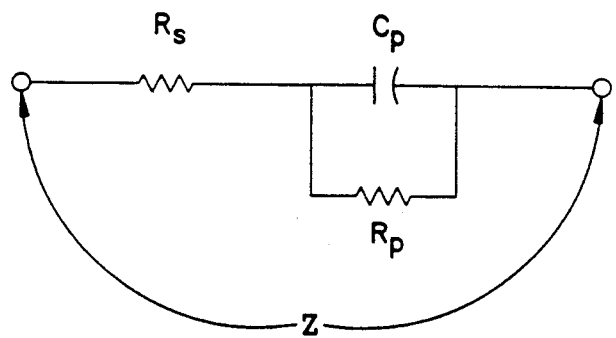
FIG. 9 is a Randle's equivalent circuit which is one of several equivalent circuits which may be used to approximate the electrical characteristics of the soil and the pipe/soil interface which are electrically connected between the metallic pipe and the buried electrode.
Figure 10:
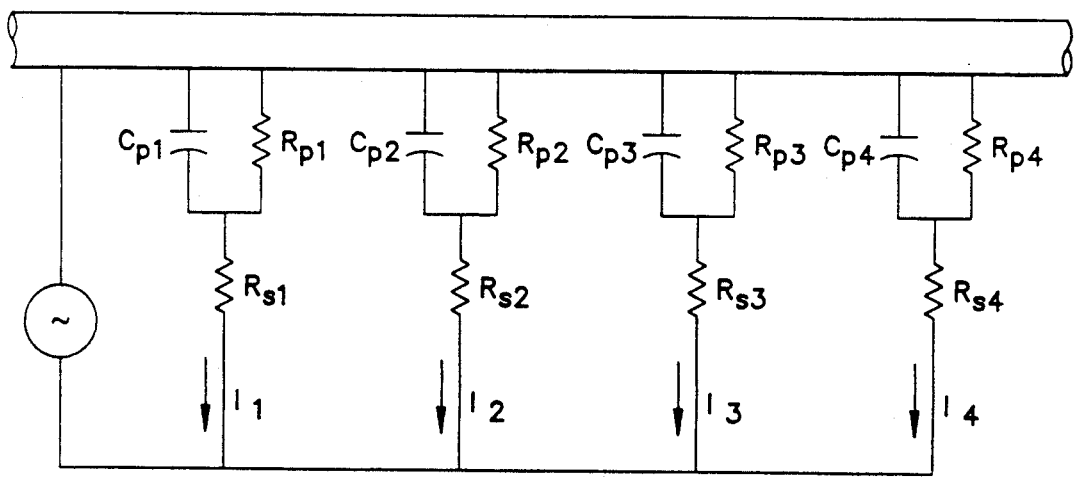
FIG. 10 illustrates the distributed nature of the resistive and capacitive elements of the equivalent circuit used to model the buried pipe.

FIG. 9 illustrates an equivalent circuit which is one of several which may be used in determining the parameters of the present invention. The parallel resistance $R_p$ and capacitance $C_p$ represent the interfacial resistance and capacitance between the metal pipe and the surrounding soil electrolyte. $R_s$ represents the series resistance through the soil. The impedance Z is the impedance seen across the terminals of these circuit elements. The distributed nature of this impedance is illustrated in FIG. 10.

FIG. 8A shows the magnitude of the impedance Z plotted as a function of frequency in the manner of a conventional Bode plot. The phase for these impedance measurements is similarly plotted in FIG. 8B. FIG. 8C shows the same data plotted in a conventional Nyquist plot.

The solid lines for each impedance plot represent the differential impedance as a function of frequency for an area having no holidays and therefore having an intact protective coating. As expected from observation of the equivalent circuit depicted in FIG. 9, at low frequencies (the right end of the Nyquist plot) the circuit is essentially the series resistance of $R_s$ plus $R_p$. Therefore it exhibits its greatest resistance and essentially zero phase shift. At high frequencies (left end of the Nyquist plot of FIG. 8C), where the capacitance $C_p$ is essentially a short circuit it exhibits essentially a resistive impedance but at a lower resistance. At intermediate frequencies the impedance is a complex function having both significant reactive and resistive components.

If the area or region of the pipeline, which is intermediate the adjacent local regions for which data is obtained in accordance with the present invention, has a holiday but no significant corrosion, then that region will exhibit a decreased resistance and a decreased capacitance. That condition is illustrated by the phantom, alternate dashed and dotted, line in each of the impedance plots.

Alternatively, if the region, which is intermediate the positions at which the differential impedance data i obtained, has a holiday which has been subjected to significant corrosion, then the corroded area will be a region of increased capacitance and a resistance which is less than that of an intact coating but greater than an uncorroded surface. This situation is shown as dashed lines in the impedance plots of FIG. 8. Under that condition the circuit would exhibit a greater essentially resistive impedance at low frequencies than it exhibited in the absence of corrosion and substantially the same essentially resistive impedance at very high frequencies. At the intermediate frequencies it would be expected to show a larger reactive component as a result of the increased capacitance.

Therefore the impedance plots may be visually analyzed and compared to get an indication of the conditions along the buried pipeline.

In the initial survey of the pipe to obtain locations of excessive transverse currents, lower frequency sources are preferred. This is because greater differential values of transverse currents are measured at lower frequencies because the capacitive reactance is considerably higher at the lower frequencies and therefore the detected current is more a function of the interfacial resistance which varies over a greater range as a function of protective cover condition. Therefore, holidays are more apparent at lower frequencies.

Thus, it can be seen from the above description that one improvement of the present invention is that magnetic detection may be used to directly detect transverse currents flowing from the pipe at local regions of the pipe. Additionally, the use of correlation discrimination techniques improve the magnetic detection of on-pipe currents which represent the compliment of transverse currents. Finally, magnetic techniques permit the localized application of electrochemical impedance techniques for determining the corrosion rate at localized positions along the pipe line. The application of correlation techniques enhances both the detection of the electrochemical impedance as well as the detection of current relationships along the pipe.

While certain preferred embodiments of the present invention have been disclosed in detail, it is to be understood that various modifications may be adopted without departing from the spirit of the invention or scope of the following claims.

We claim:

1. A non-invasive method for detecting electrical current flow characteristics in a circuit having local regions of an electrically conductive object buried in an electrolyte, the method comprising:
   (a) impressing an electrical potential, which is alternating at at least one selected frequency, between the buried object and an electrode which is buried in the electrolyte and spaced from the object the object being a metallic object subject to corrosion in the electrolyte and the impressed potential causing perturbations of ambient currents, the perturbations being sufficiently small to avoid significant depolarization of the corroding object/electrolyte interface away from its steady state in its ambient environment; and
   (b) detecting the alternating magnetic field induced by electrical currents which are injected into said circuit by the electrical potential and are distributed in the electrolyte at a local region of the circuit and flow transversely away from the pipe, the field being detected along at least one selected spatial axis at the frequency of potential impression.

2. A method in accordance with claim 1 wherein the magnetic field at each local position is detected by detecting the magnetic field at each of at least two places which are at two different radii from the pipe and then subtracting one from the other to eliminate ambient magnetic fields such as geomagnetic fields.

3. A method in accordance with claim 1 wherein the object is an elongated pipe buried in a soil and the magnetic field is detected along parallel axes at a plurality of spaced local positions longitudinally along the pipe and wherein the detected magnetic field at adjacent local positions are differenced to obtain the field differential between those local positions and to eliminate common magnetic noise such as geomagnetic fields.

4. A method in accordance with claim 1 wherein the field is detected along at least three, three dimensionally arranged axes to simultaneously detect current components in all three dimensions and wherein the detected magnetic field at adjacent local longitudinally spaced positions along the pipe are differenced to obtain the field differential between those local positions and to eliminate common magnetic noise such as geomagnetic fields.

* * * * *